United States Patent [19]

Dubler et al.

[11] Patent Number: 5,239,086

[45] Date of Patent: Aug. 24, 1993

[54] HAPTENS AND TRACERS FOR IMMUNOASSAYS FOR PROPOXYPHENE

[75] Inventors: Robert E. Dubler, Gurnee; Jonathan Grote, Grayslake; Donna R. Kuhn, Prospect Heights, all of Ill.

[73] Assignee: Abbott Laboratories, Abbott Park, Ill.

[21] Appl. No.: 736,890

[22] Filed: Jul. 29, 1991

[51] Int. Cl.$^5$ .......................................... C07D 311/86
[52] U.S. Cl. ................................... 549/223; 560/173; 560/177; 560/194
[58] Field of Search ................ 549/223; 560/173, 177, 560/194

[56] References Cited

U.S. PATENT DOCUMENTS 4,025,501 5/1977 Leute ................................ 424/12 X

OTHER PUBLICATIONS

"Measurement of Dextropropoxyphene and Nordextropropoxyphene in Biological Fluids", by R. J. Flanagan et al., *Human Toxicol,* 3, 103S-114 S (1984).

"Detection of Methadone and Propoxyphene in Stored Tissue", by M. G. Fransioli et al., *Journal of Analytical Toxicology,* vol. 4, Jan./Feb. 1980, pp. 46-48.

*Primary Examiner*—Richard L. Raymond
*Attorney, Agent, or Firm*—Gregory W. Steele; Lawrence S. Pope; Thomas M. Breininger

[57] ABSTRACT

Disclosed is a substantially optically pure hapten, useful in an immunoassay for dextropropoxyphene and/or nordextropropoxyphene. The hapten corresponds to a specified structural formula (IX).

Also disclosed is an immunogen derived from the hapten as well as an antibody raised in response to an immunogen derived from the hapten.

Also disclosed is a fluorescent tracer derived from a substantially optically pure compound corresponding to the hapten, the tracer being useful in an immunoassay for dextropropoxyphene and/or nordextropropoxyphene.

Also disclosed is an improved immunoassay for determining dextropropoxyphene and/or nordextropropoxyphene in a biological sample involving a step of contacting the sample with antibodies raised in response to the immunogen. Also disclosed is a fluorescence polarization immunoassay (FPIA) for determining dextropropoxyphene and/or nordextropropoxyphene involving a step of contacting the sample with antibodies raised in response to the immunogen, and/or involving a step of contacting the sample with a fluorescent tracer.

7 Claims, No Drawings

HAPTENS AND TRACERS FOR IMMUNOASSAYS FOR PROPOXYPHENE

BACKGROUND OF THE INVENTION

1. Technical Field

The present invention is directed to reagents and methods for performing an immunoassay, particularly a fluorescence polarization immunoassay (FPIA), to determine the presence and/or amount of dextropropoxyphene and/or the principal metabolite of dextropropoxyphene (namely, nordextropropoxyphene) in samples, particularly aqueous, fluid biological samples such as urine, blood serum or blood plasma, and to an immunoassay based on the reagents. More particularly the invention is directed to new haptens, immunogens prepared from the haptens, antibodies raised against the haptens and immunoassays which utilize reagents and methods of the invention.

2. Background

Dextropropoxyphene is a narcotic analgesic which has found wide therapeutic use. Unfortunately, however, it has also become a drug of abuse. Dextropropoxyphene is also known by the following chemical names: [S-(R*,S*)]-alpha-[2-(Dimethylamino)-1-methylethyl]-alpha-phenylbenzeneethanol propanoate (ester); alpha-d-4-Dimethylamino-3-methyl-1,2-diphenyl-2-butanol propionate; (+)-1,2-Diphenyl-2-propionoxy-3-methyl-4-dimethylaminobutane; (+)-4-Dimethylamino-1,2-diphenyl-3-methyl-2-propionyloxybutane; alpha-d-4-Dimethylamino-3-methyl-1,2-diphenylbutan-2-ol propionate; and d-propoxyphene. Dextropropoxyphene corresponds to the following structural formula:

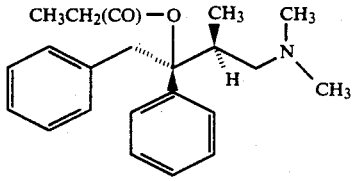

Dextropropoxyphene

As reported by R. J. Flanagan et al in "Measurement of Dextropropoxyphene and Nordextropropoxyphene in Biological Fluids", *Human Toxicol.* (1984), 3, 103S-114S, various methods have been explored for detecting, identifying and measuring the amount of dextropoxyphene and its principal plasma metabolite, nordextropropoxyphene. Examples of such methods include thin-layer chromatography (TLC) and gas-liquid chromatography (GLC) of solvent or solid-phase extracts of urine or gastric contents, as well as a homogeneous enzyme immunoassay method.

U.S. Pat. No. 4,025,501 is directed to compounds for conjugation to antigens for the production of antibodies which recognize (d,l)-propoxyphene and its metabolites in immunoassays. The compounds to which this patent is directed are prepared by reacting 1,2-diphenyl-3-methyl-4-dimethylamino-2-butanol with a dibasic acid to form a half-acid ester, the acid group of which is disclosed as being activated for conjugation to amino groups of proteins or polypeptides.

However, presently existing assays for propoxyphene tend to suffer from disadvantageously high cross-reactivities for various structurally similar compounds. The present invention has a number of objects. They include, for example, providing new haptens, immunogens prepared from the haptens, and antibodies raised in response to the immunogens, suitable for use in immunoassays which are highly discriminating for dextropropoxyphene and its principal metabolite, nordextropropoxyphene, in which immunoassays cross-reactivity for interfering compounds such as methadone and chlorphenoxamine, among others, is minimized or substantially eliminated.

Additionally, presently existing assays for propoxyphene involve the use of racemic mixtures of molecules for preparation of immunogens to raise antibodies against propoxyphene. However, propoxyphene can exist in four different isomeric forms because of the presence of two optically active centers within the molecule. Thus, utilization of such racemic mixtures for the preparation of immunogens to raise antibodies is believed to result in the production of at least four types of antibodies of which only about 25% will detect the optical form of propoxyphene that is relevant to the assay. The form of propoxyphene which is available on the market is an optically active form of the drug. Moreover, of the four isomeric forms of propoxyphene, there is only one form which appears to have any substantial efficacy in man, namely dextropropoxyphene. Accordingly, particularly for quantitative assays for that form of propoxyphene having efficacy in man, and/or for its most important metabolite, it would be desirable to provide antibodies, a larger proportion of which are reactive to the effective form of the drug than to ineffective forms of the drug.

The present invention is related to immunoassays, particularly competitive immunoassays, involving reagents and techniques particularly suitable for determining the presence and/or amount of dextropropoxyphene and/or nordextropropoxyphene in biological fluids. The present invention can provide, among others, an advantage of allowing for an advantageously effective determination of the amount of dextropropoxyphene and/or its principal metabolite, nordextropropoxyphene, with minimization of interference from other related compounds. The present invention is in part based on new, substantially optically pure haptens, which can be utilized in the preparation of immunogens and/or tracers suitable for use in immunoassays.

SUMMARY OF THE INVENTION

The invention provides for a substantially optically pure hapten, useful in an immunoassay for dextropropoxyphene and/or nordextropropoxyphene. The hapten of the invention corresponds to the structural formula (IX):

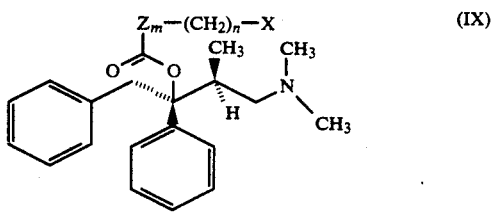

In formula (IX), Z is a —NH— moiety and is present when m=1. X is a functional group selected from the group consisting of —CHO, —COOH, —NH$_2$, and —COOR in which R is a C$_1$–C$_3$ alkyl group. In formula (IX), m can equal 0 or 1, and n can equal an integer of from 1 to 3.

The invention also provides for an immunogen derived from a hapten of the invention.

The invention also provides for an antibody raised in response to an immunogen derived from a hapten of the invention.

The invention also provides for a fluorescent tracer derived from a substantially optically pure compound of the invention, the tracer being useful in an immunoassay for dextropropoxyphene and/or nordextropropoxyphene. The substantially optically pure compound corresponds to the hapten defined in formula (IX).

The invention also provides for an improved immunoassay for determining the presence or amount of dextropropoxyphene and/or nordextropropoxyphene in a biological sample. The improved immunoassay comprises a step of contacting the sample with an antibody (or antibodies) raised in response to an immunogen of the invention. Moreover, the invention provides for a fluorescence polarization immunoassay (FPIA) for determining the presence or amount of dextropropoxyphene and/or nordextropropoxyphene in a biological sample. The FPIA comprises a step of contacting the sample with antibodies raised in response to an immunogen of the invention, and/or comprises a step of contacting the sample with a fluorescent tracer of the invention.

DETAILED DESCRIPTION OF THE INVENTION

A hapten of the invention is substantially optically pure, and is particularly useful in an immunoassay for dextropropoxyphene and/or for nordextropropoxyphene, a metabolite of dextropropoxyphene. As used herein, the phrase "substantially optically pure" means that the product hapten contains less than or equal to 10 percent, preferably less than or equal to 5 percent, and most preferably less than or equal to 2 percent, by weight of the dextrorotatory (d or +) enantiomer of the hapten based on the sum by weight of the dextrorotatory and levorotatory (1 or −) enantiomers. A hapten of the invention corresponds to the formula (IX):

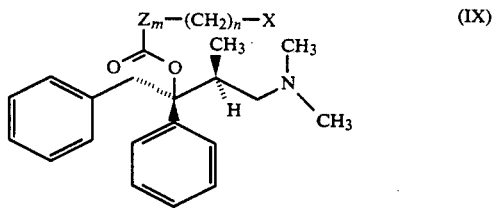

In formula (IX), Z represents a divalent —NH— moiety and is present when m=1. X is a functional group selected from the group consisting of —CHO, —COOH, —NH$_2$, and —COOR in which R is a C$_1$-C$_3$ alkyl group. It is preferred that X be an aldehyde group. It is also preferred that R be an ethyl group. In formula (IX), m can equal 0 or 1, preferably 0, and n can equal an integer of from 1 to 3, preferably 3. The functional group, X, in formula (IX) is a functional group suitable for utilization, for example, in attaching an antigenicity-conferring moiety to the hapten, for example, by reaction directly, or via an intermediate step, with a co-reactive functional group from an antigenicity-conferring carrier.

Haptens of the invention can be prepared by the following illustrative general procedures. Typically, the optically active dextropropoxyphene derivatives (haptens) of the invention are prepared by reaction of dextropropoxyphene hydrochloride with a suitable reducing agent. The resulting alcohol is then derivatized by treatment with an acyl halide or isocyanate reagent, which contains a second functionality capable of being transformed into another functional group. This new functional group allows the dextropropoxyphene derivative thereby produced to be coupled to antigenic molecules. The second functionality can be an ester or an olefin. The overall methodology used for elaboration of the linkage of the dextropropoxyphene derivative in this manner is central to the obtainment of haptenic dextropropoxyphene derivatives of high optical purity.

Reducing agents which can be used in the preparation of haptens of the invention include reducing agents such as lithium aluminum hydride, di-isobutylaluminum hydride, bis(methoxyethoxy)aluminum hydride, and the like, with lithium aluminum hydride being preferred.

The acyl halide or isocyanate reagents described above are preferably aliphatic acid chlorides or aliphatic isocyanates such as pentenoyl chloride, butenoyl chloride, ethyl isocyanatoacetate, ethyl 3-isocyanatopropionate and the like, with pentenoyl chloride being preferred for hapten formation. Acid chlorides and isocyanates derived from aromatic acids are less preferred.

Modification of the second functionality present in the acid halide molecule to allow for coupling to an antigenic molecule utilizes two types of reagents, depending on the type of functionality present. Unsaturated acid chlorides, such as butenoyl chloride, give rise to dextropropoxyphene derivatives containing an olefin. Olefins can be transformed to aldehydes using a variety of oxidizing reagents, including lead tetraacetate, sodium periodate, ozone followed by a suitable reductive workup, and the like. Unsaturated isocyanates also give rise to olefinic dextropropoxyphene derivatives which contain acids upon treatment with suitable cleavage reagents. These reagents include acid, base, aromatic sulfide salts, silyl iodides, and the like. Acid chlorides containing a second ester functionality also can give rise to dextropropoxyphene derivatives containing an acid.

Both the dextropropoxyphenic aldehydes and acids obtained are linked to antigenic molecules by methods well known to those skilled in the art.

It has been found that fluorescence polarization immunoassays performed utilizing antisera raised from immunogens prepared from haptens of the invention can provide a particularly high specificity for dextropropoxyphene and/or nordextropropoxyphene and an especially low cross-reactivity for interfering compounds such as methadone and chlorophenoxamine, among others.

An immunogen of the invention is derived from a substantially optically pure hapten of the invention. An immunogen of the invention is particularly useful in an immunoassay for dextropropoxyphene and/or nordextropropoxyphene. The immunogen corresponds to the formula (X):

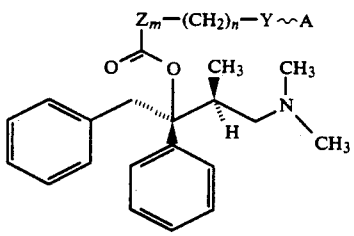

$$Z_m-(CH_2)_n-Y\sim A \qquad (X)$$

wherein Z is as defined for the hapten corresponding to formula (IX) above. Y in formula (X) is a divalent moiety for linking for $(CH_2)_n$ group to the antigenicity-conferring moiety A. Y can be —NH—, —(CO)NH—, or —NH(CO)— with —NH— being preferred. It is to be understood that wherever in the specification and claims herein, a divalent moiety for linking two other structures together is specified, e.g., —(CO)NH— as Y for linking $(CH_2)_n$ and A, the left hand portion of the divalent moiety is attached to the structure on the left and the right hand portion is attached to the structure on the right ((i.e., for this example $(CH_2)_n$—(CO)N-H—A)). In formula (X), the subscript, m, can be 0 or 1, with 0 being preferred, and the subscript n can be an integer of from 1 to 3 with 3 being preferred. The antigenicity-conferring carrier moiety, A, can be selected from a wide variety of antigenicity-conferring carrier moieties. As can be appreciated from formula (X), the moiety A represents the residue of an antigenicity-conferring carrier bound via Y to the haptenic portion of the immunogen of formula (X).

Covalent linkage of the haptenic materials described herein to antigenicity-conferring materials can be accomplished by methods well known in the art, the choice of which will be dictated by the nature of the linking functionality in the dextropropoxyphene derivative (i.e., X in formula (IX)) and the carrier chosen for the linkage.

Typically, the antigenicity-conferring carrier moiety, A, is provided by reacting the functional group X of a hapten corresponding to formula (IX) with a co-reactive functional group of an antigenicity-conferring carrier such as, for example, a naturally occurring or synthetic poly(amino-acid) by generally known preparative techniques. Typically, in preferred embodiments of the invention, the naturally occurring poly(amino-acid), bovine thyroglobulin (BTG), is utilized as the antigenicity-conferring carrier to provide the moiety, A, in structural formula (X), but it is to be understood that other protein carriers can be utilized, including for example, albumins and serum proteins such as globulins, lipoproteins, ocular lens proteins, and the like. Some illustrative antigenicity-conferring protein carriers include bovine serum albumin (BSA), keyhole limpet hemocyanin (KLH), egg ovalbumin, bovine gamma globulin (BGG), thyroxine binding globulin, etc. Alternatively, synthetic poly(amino-acids) can be utilized such as polylysine, etc.

For example, a hapten in which X of formula (IX) is carboxyl, can be coupled to bovine serum albumin, preferably under conditions normally used to form amide bonds which conditions are well known to those skilled in the art, by utilizing as the coupling agent, for example, a carbodiimide, especially a water soluble carbodiimide such as 1-ethyl-3-(3-dimethylaminopropyl) carbodiimide (EDC) or 1-cyclohexyl-3-(2-morpholinoethyl) carbodiimide metho-p-toluenesulfonate.

The same reagents can be used in the case where X of the hapten is a —NH₂ group, in which case an amide bond is formed with a carboxyl group on the bovine serum albumin. When Q of the hapten is —CHO, the aldehyde can be reductively aminated to a corresponding amine functional group. Other transformations of the aldehyde into useful haptens are obvious to one skilled in the art.

Antibodies of the present invention are prepared by developing an immune response in animals to immunogens of the invention. The immunogen is administered to animals such as rabbits, mice, rats, sheep or cows by a series of injections according to techniques generally known in the art. An antibody, according to the present invention, is raised in response to an immunogen of the invention which is derived from a substantially optically pure hapten of the invention. Both polyclonal and monoclonal antibodies recognize specific epitopes on an immunogen, and, while typically polyclonal antibodies have been utilized in the present invention, both may be suitable. Polyclonal antibodies consist of a mixture of multiple antibodies, each recognizing a specific epitope, whereas monoclonal antibodies are produced by cells secreting a single antibody recognizing a specific epitope. Techniques for preparing polyclonal antibodies generally are well known in the art.

Monoclonal antibodies may be prepared by injecting animals, such as mice or rats, intraperitoneally, subcutaneously, intravenously, or in some other manner, with an antigen, namely an immunogen corresponding to formula (X) above, to elicit an immune response in the animals (namely, the production of antibodies which are specific for the antigen). Sera from the animals are drawn, and the sera are tested to determine the titer of antibody in the sera (to determine whether or not the animal elicited the desired immune response, and to what extent). Those animals in which the desired immune response has been produced are permitted to rest for approximately two to three months. After this two-month to three-month period of time, and approximately three days prior to the anticipated fusion of B-lymphocyte cells (cells which, upon stimulation by antigen, mature into plasma cells which synthesize antibody, and which are also referred to as B cells) with myeloma cells (tumor cells), a boost injection of the antigen is administered to these animals. B-lymphocyte cells are then removed from the spleens of these animals by standard procedures, and the B-lymphocyte cells are then fused with myeloma fusion partners according to standard procedures, such as those described in Kohler and Milstein, "Continuous Culture of Fused Cells Secreting Antibody of Predefined Specificity," *Nature*, 256, 495 (1975). The B-lymphocyte-myeloma fusions are then plated in multiwell tissue culture plates containing HAT media, or other suitable media. The resulting cultures are fed with HT media, or other suitable media, and fetal bovine serum or calf bovine serum on or about the fifth and seventh days after the fusion of the cells and then tested on or about the tenth day after the fusion for the presence of antibody which is specific for the antigen. Specific desirable hybrids are then cloned by limiting dilution. (Hybrid cells are diluted in differing amounts of HT media, or other suitable media, and plated out in tissue culture plates in order to isolate a single desired clone.) Established clones are then retested for specificity to a broader panel of cross reactants.

The amount of the resulting monoclonal antibodies produced by a desired clone can then be scaled up to produce a sufficient quantity of antibody for purification in either: (1) tissue culture (by expanding the number of cells in tissue culture, or HT media); or (2) mice for ascites. The monoclonal antibodies can be scaled up in mice by injecting hybrid cells into the abdominal cavity of mice and allowing the cells to grow (usually for about 7 days). The ascites is harvested from the mice by sacrificing the mice, collecting the ascites fluid, and purifying the ascites fluid. BALB/c mice are the most common strain of laboratory mouse used for this process, and they can be obtained from any mouse vendor. Pristane, should be injected into the mice to stimulate their immune systems to produce B and T cells (about two or three weeks before the hybrid cells are injected into the mice) which serve as a feeder layer for the clone cells that are injected into the mice. This is performed to provide a suitable environment in which the hybrid cells can grow.

The invention also provides for improved immunoassays for determining the presence or amount of dextropropoxyphene and/or nordextropropoxyphene in biological samples. An improved immunoassay of the invention includes (comprises) a step of contacting the sample to be determined with antibodies raised in response to an immunogen of the invention. It is contemplated that any immunoassays for propoxyphene and/or nordextropropoxyphene utilizing haptens, immunogens, and/or antibodies raised against immunogens, according to the invention, are within the scope of the present invention. Examples of immunoassays include radioimmunoassays (RIAs), enzyme immunoassay (EIAs), enzyme linked immunosorbent assays (ELISAs) and fluorescent polarization immunoassays (FPIAs). In a fluorescent polarization immunoassay (FPIA), a fluorescent tracer of the invention may be utilized either with or without utilization of antibodies raised in response to an immunogen of the invention.

A fluorescent tracer of the invention can be thought of as being derived from a substantially optically pure compound corresponding to a hapten of the invention. A tracer of the invention is useful in an immunoassay for dextropropoxyphene and/or nordextropropoxyphene and corresponds to the formula (XI):

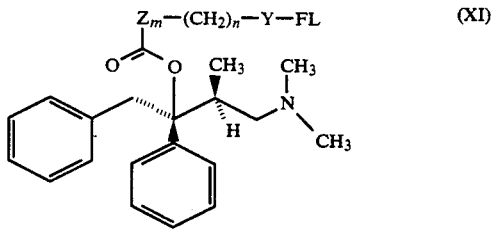

(XI)

wherein Z is as defined for the hapten corresponding to formula (IX) above with subscript m equal to 0 or 1, preferably 1. In formula (XI), Y is a divalent radical selected from —NH—, —(CO)NH—, and —NH(CO)— with —(CO)NH— being preferred. The subscript n is an integer of from 1 to 3 and is equal to 1 in a preferred tracer of the invention. In formula (XI), FL is a fluorescence-conferring moiety, and Y serves to link the fluorescence-conferring moiety, FL, to the divalent radical —(CH$_2$)$_n$—. The fluorescence-conferring moiety, FL, can be selected from a variety of fluorescence-conferring moieties.

As can be appreciated from formula (XI), the moiety FL represents the monovalent residue of a fluorescence-conferring compound bound via Y to the remainder of the tracer. In preferred embodiments of the invention, the fluorescence-conferring moiety of the fluorescent tracer is a monovalent residue of fluorescein or a monovalent residue of a fluorescein derivative. By way of example, any of the following fluorescein derivatives can be utilized: FL—NH$_2$, fluorescein amine; FL—CH$_2$NH$_2$, aminomethylfluorescein; and FL—COOH, carboxyfluorescein. As used herein, FL stands for a fluorescein moiety corresponding to the following formula (XII):

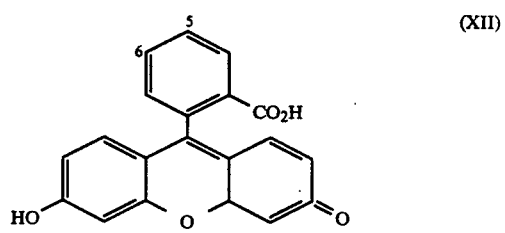

(XII)

In a preferred embodiment of the invention, FL—NH$_2$ is utilized for preparation of the tracer, preferably wherein the —NH2 group is bonded to FL at either the number 5- or 6-position (see FIG. XII above), typically at the 5-position.

Tracers of the invention generally can be prepared by linking an appropriate fluorescent compound to a hapten of the invention represented by formula (IX) above in which X represents a functional group suitable for utilization in attaching the fluorescent compound to the hapten, for example, by reaction directly, or via an intermediate step, with a co-reactive functional group from the fluorescent compound. Examples of functional groups for the hapten include: —COOH, —NH$_2$, and —COOR in which R is a C$_1$-C$_3$ alkyl group. Reaction conditions for reacting such functional groups of the hapten as represented by X with co-reactive functional groups of a fluorescent compound are well known in the art.

Normally, competitive binding immunoassays are utilized according to the method of the invention to determine the presence and/or amount of dextropropoxyphene and/or nordextropropoxyphene in a biological sample. Typically, competitive binding immunoassays are used for measuring ligands in a test sample. For purposes of this disclosure, a "ligand" is a substance of biological interest (dextropropoxyphene and/or nordextropropoxyphene) to be quantitatively determined by a competitive binding immunoassay technique. The ligand competes with a labeled reagent (a "ligand analog" or "tracer") for a limited number of ligand binding sites on antibodies specific to the ligand and ligand analog (herein, antibodies prepared in response to an immunogen of the invention). The concentration of ligand in the sample determines the amount of ligand analog which binds to the antibody, and the amount of ligand that will bind to the antibody is inversely proportional to the concentration of ligand in the sample, because the ligand and the ligand analog each bind to the antibody in proportion to their respective concentrations.

In one embodiment of the invention, fluorescence polarization immunoassay (FPIA) techniques are utilized for determining the amount of tracer-antibody conjugate produced in a competitive binding immunoassay. Such procedures are based on the principle that a fluorescent labeled compound, when excited by plane polarized light, will emit fluorescence having a degree of polarization inversely related to its rate of rotation. Accordingly, when a tracer-antibody conjugate having a fluorescent label is excited with plane polarized light, the emitted light remains highly polarized because the fluorophore is constrained from rotating between the time that light is absorbed and emitted. In contrast, when an unbound tracer is excited by plane polarized light, its rotation is much faster than the corresponding tracer-antibody conjugate and the molecules become more randomly oriented. As a result, the light emitted from the unbound tracer molecules is depolarized.

More specifically, a preferred FPIA method of the present invention for determining the presence or amount of dextropropoxyphene and/or nordextropropoxyphene in a sample comprises the steps of: (a) contacting a sample with: (1) an antiserum containing monoclonal or polyclonal, typically polyclonal, antibodies which have been raised in response to an immunogen of the invention; and (2) a fluorescent tracer of the invention, the fluorescent tracer being capable of producing a detectable fluorescence polarization response to the presence of the antiserum; (b) passing plane polarized light through the resulting solution from step (a) to obtain a fluorescence polarization response; and (c) detecting the fluorescence polarization response of the solution of step (b) as a measure of the presence or amount of dextropropoxyphene and/or nordextropropoxyphene in the sample.

By maintaining constant the concentration of fluorescent tracer and antibody, the ratio of dextropropoxyphene and/or nordextroproxyphene-antibody complex to fluorescent tracer-antibody complex that is formed is directly proportional to the amount of dextropropoxyphene and/or nordextropropoxyphene in the sample. Upon exciting the mixture with linearly polarized light and measuring the polarization (in units of millipolarization) of the fluorescence emitted by a fluorescent tracer and a fluorescent tracer-antibody complex, one is able to quantitatively determine the amount or qualitatively determine the presence of dextropropoxyphene and/or nordextropropoxyphene in the sample.

The results can be quantified in terms of net millipolarization units and span (in millipolarization units). The measurement of net millipolarization units indicates the maximum polarization when a maximum amount of the fluorescent tracer is bound to the antibody, in the absence of any dextropropoxyphene and/or nordextropropoxyphene. The higher the net millipolarization units, the better the binding of the tracer to the antibody. The assay span is the difference between the net millipolarization values obtained when the maximum amount of tracer is bound in the absence of any dextropropoxyphene and/or nordextropropoxyphene and the net millipolarization obtained when a specific amount of dextropropoxyphene and/or nordextropropoxyphene is present in the sample. A larger span allows for more millipolarization units to be placed between each of the calibrators of the standard curve generated for the assay, thereby providing better assay precision which, in turn, results in a better numerical analysis of the data obtained. It is important to note that the span varies depending on the sample size used which, in turn, may alter the preferred combination.

Fluorescent tracers of the present invention are substantially optically pure. These tracers have the particular advantage in instances where antisera based on polyclonal antibodies are utilized. Because dextropropoxyphene is essentially optically pure in the body, the use of tracers which are substantially optically pure in combination with antibodies derived from substantially optically pure immunogens have been found to allow for an enhanced signal across the chosen dynamic range in a dextropropoxyphene and/or nordextropropoxyphene assay utilizing FPIA techniques. One resultant advantage is that FPIA assays of the present invention can achieve sensitivities of the order of 20.0 nanograms/milliliter (ng/ml) of dextropropoxyphene and/or nordextropropoxyphene in the sample.

Some significant features of the most preferred combination of fluorescent tracer of the present invention and immunogen of the present invention include: (1) the high degree of specificity of the antibodies, generated in response to the immunogen, for dextropropoxyphene and/or nordextropropoxyphene, and (2) minimal cross reactivity of these antibodies to potential interferants.

The pH at which an FPIA method of the present invention is practiced must be sufficient to allow the fluorescein moiety of the fluorescent tracer to exist in its open form. The pH may range from about 3 to 12, more usually in the range of from about 5 to 10, most preferably from about 6 to 9. Various buffers may be used to achieve and maintain the pH during the FPIA procedure. Representative buffers include borate, phosphate, carbonate, tris, barbital, citrate and the like. The particular buffer employed is not critical to the present invention, but the tris, phosphate and citrate buffers are preferred. The cation portion of the buffer will generally determine the cation portion of the tracer salt in solution.

Riboflavin binding protein (RBP) is added to the sample or to one or more of the assay reagents to bind any riboflavin present in the sample into RBP-riboflavin complexes, thus eliminating potential fluorescence interference. RBP is a protein of approximately 32,000 M.W. which is isolated from egg whites. Upon isolation from the egg, each molecule of RBP contains one molecule of riboflavin. This, the holoprotein form of RBP, must be converted to the apoprotein form by dialysis, under acidic conditions, to remove the bound riboflavin. The RBP apoprotein utilized in the present invention is commercially available from Sigma Chemical Company, St. Louis, Mo. The amount used is not critical, provided a sufficient quantity is used to bind all free riboflavin in the sample.

A fluorescent polarization immunoassay of the present invention is a "homogeneous assay," which means that the end polarization readings are taken from a solution in which bound tracer is not separated from unbound tracer. This is a distinct advantage over heterogeneous immunoassay procedures, such as those where the bound tracer must be separated from the unbound tracer before a reading can be taken.

The reagents for the fluorescence polarization assay of the present invention comprise: (1) polyclonal or monoclonal, typically polyclonal, antibodies, for dextropropoxyphene; and (2) fluorescent tracer reagent.

Additionally, largely conventional solutions including a pretreatment solution, a dilution buffer, dextropropoxyphene calibrators and dextropropoxyphene controls are desirably prepared. Typical solutions of these reagents, some of which are described below, are commercially available in assay "kits" from Abbott Laboratories, Abbott Park, Ill.

All percentages expressed herein are weight/volume unless otherwise indicated. The preferred reagents, calibrators and controls for a preferred fluorescence polarization immunoassay of the present invention can be found in Example 7 infra.

The preferred FPIA procedure is especially designed to be used in conjunction with the Abbott TD$_X$® Clinical Analyzer, the Abbott TD$_X$FL$_X$™ or the Abbott AD$_X$® Drugs of Abuse System, all three of which are available from Abbott Laboratories, Abbott Park, Ill. The calibrators, controls, or unknown samples are pipetted directly into the sample well of the TD$_X$® sample cartridge. One of the advantages of this procedure is that the sample does not require any special preparation. The assay procedure from this point is fully automated.

If a manual assay is being performed, the sample is mixed with the pretreatment solution in dilution buffer and a background reading is taken. The fluorescence tracer is then mixed with the assay. The antibody is then finally mixed into the test solution. After incubation, a fluorescence polarization reading is taken.

The fluorescence polarization value of each calibrator, control or sample is determined and is printed on the output tape of an instrument, such as the Abbott TD$_X$® Analyzer, TD$_X$FL$_X$™ or AD$_X$® System. A standard curve is generated in the instrument by plotting the polarization of each calibrator versus its concentration using a nonlinear regression analysis. The concentration of each control or sample is read off of the stored calibration curve and printed on the output tape.

With respect to the foregoing preferred procedure, it should be noted that the tracer, antibody, pretreatment solution, wash solution, calibrators and controls should be stored between about 2 degrees C. and about 8 degrees C. while the dilution buffer should be stored at ambient temperature. A standard curve and controls should be run every two weeks, with each calibrator and control run in duplicate. All samples can be run in duplicate.

The following examples are provided to further illustrate embodiments of the invention and should not be construed as a limitation on the scope of the invention.

The following general experimental procedures were utilized in the preparation of the haptens of the following examples.

EXAMPLE 1

This example illustrates the preparation of (2S,3R)-4-Dimethylamino-1,2-diphenyl-3-methyl-butan-2-ol, corresponding to formula (I) below, for use in the preparation of haptens and tracers of the invention.

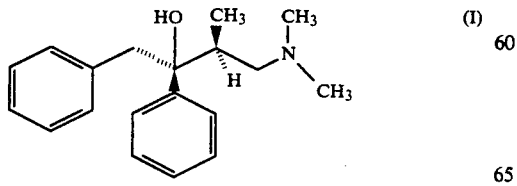

(I)

To a cooled (0° C.) suspension of 200 milligrams (mg, 0.53 mmol) of dextropropoxyphene hydrochloride in 3.0 milliliters (ml) of anhydrous tetrahydrofuran (THF) was added 22 mg (0.59 mmol) of lithium aluminum hydride. The mixture was warmed to ambient temperature and stirred for 4 hours (hr). The reaction was then quenched with water, basified with 2 molar (M) aqueous potassium hydroxide solution, and extracted 3 times with 10 ml aliquots of ethyl acetate. The combined extracts were dried over MgSO$_4$, filtered, and concentrated to 164 mg of a clear colorless oil of (2S,3R)-4-Dimethylamino-1,2-diphenyl-3-methyl-butan-2-ol, which was used subsequently without further purification.

EXAMPLE 2

This example illustrates the preparation of (2S,3R)-4-Dimethylamino-1,2-diphenyl-3-methyl-2-ethoxycarbonylmethylaminocarbonyloxy)-butane, corresponding to formula (II) below.

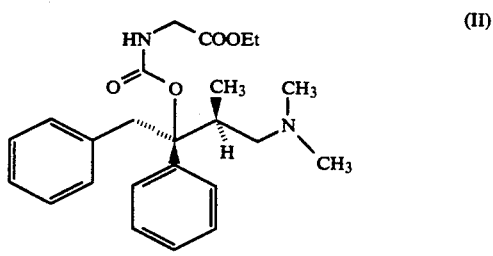

(II)

A solution of 127 mg (0.45 mmol) of the clear colorless oil (of the alcohol) prepared immediately above in a mixture of 1.0 ml benzene and 1.0 ml toluene was fractionally distilled, and only 1.0 ml of distillate was collected. The residual solution was cooled, and 0.15 ml (1.34 mmol) of ethyl isocyanatoacetate, OCN—CH$_2$COOCH$_2$CH$_3$, was injected. The resulting solution was refluxed for 1 hr, cooled and quenched with 2 drops of water. The resulting mixture was concentrated on a rotary evaporator and chromatographed directly on a 1×18 centimeter (cm) column of silica gel, packed with chloroform and eluted with 50 ml aliquots of 2%, 6%, and 10% by volume solutions, respectively, of methanol in chloroform. A total of 269 mg of a clear colorless oil of the ester (2S,3R)-4-Dimethylamino-1,2-diphenyl-3-methyl-2-(ethoxycarbonylmethylaminocarbonyloxy)-butane was obtained.

EXAMPLE 3

This example illustrates the preparation of (2S,3R)-4-Dimethylamino-1,2-diphenyl-3-methyl-2-(carboxymethylaminocarbonyloxy)-butane, corresponding to formula (III) below, a hapten of the invention.

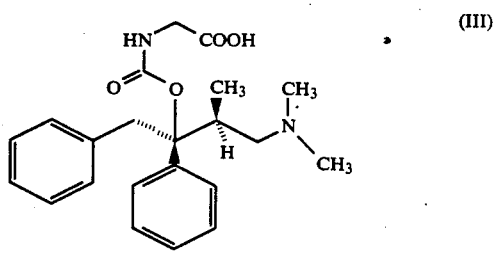

(III)

Potassium hydroxide (24 mg, 0.43 mmol) was added to a solution of 118 mg (0.29 mmol) of the clear colorless oil of the ester (prepared in Example 2 above) in a mixture of 0.75 ml tetrahydrofuran and 0.75 ml water. The solution was stirred for 12 hr at ambient temperature, acidified to pH 7, and concentrated. The concentrate was redissolved in methanol and the solution streaked onto two 0.50 millimeter (mm)×20 cm×20 cm plates, which were developed with 30% by volume solution of methanol in chloroform (methanol/chloroform). The product was eluted from the pulverized, scraped band with 80% methanol/chloroform, and concentrated to 50 mg of a white solid of the acid (2S,3R)-4-Dimethylamino-1,2-diphenyl-3-methyl-2-(carboxymethylaminocarbonyloxy)-butane.

EXAMPLE 4

This example illustrates the preparation of (2S,3R)-4-Dimethylamino-1,2-diphenyl-3-methyl-2-(5-fluoresceinylaminocarbonylmethylaminocarbonyloxy)-butane, corresponding to formula (IV) below, a tracer of the invention.

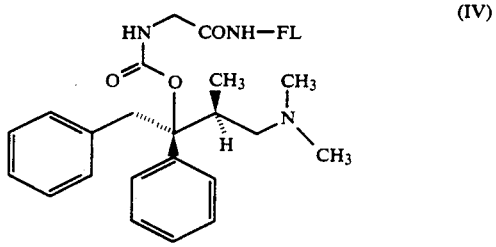

To a cooled (0° C.) solution of 3.6 mg (9.3 micromole, μmol) of the white solid acid, of Example 3 above, in 100 microliters (μl) of dimethylformamide, was added 1.2 μl (9.3 μmol) isobutyl chloroformate. The resulting solution was stirred for 1 hr, allowing warming to ambient temperature, and was then recooled to 0° C. 5-Fluoresceinamine (3.2 mg, 9.3 μmol) was then added, and the resulting solution was stirred for 12 hr at ambient temperature. The mixture was concentrated, redissolved in methanol, and streaked onto a 0.25 mm×20 cm×20 cm plate. Development with 20% methanol/chloroform, and elution of the pulverized band with 80% methanol/chloroform, provided 8.1 mg of an orange solid. This solid was rechromatographed on an additional 0.25 mm plate, eluting with 70:30:2 chloroform:methanol:glacial acetic acid. The band was pulverized and eluted with 80% methanol/chloroform to provide 32 mg of an orange solid. This solid was rechromatographed twice more on additional 0.25 mm plates, developed with 50% methanol/chloroform each time, and each pulverized band was eluted with 80:20:1 methanol:chloroform:concentrated ammonium hydroxide. 4.5 mg of an orange solid of (2S,3R)-4-Dimethylamino-1,2-diphenyl-3-methyl-2-(5-fluoresceinylaminocarbonylmethylaminocarbonyloxy)-butane, was obtained after the final purification.

EXAMPLE 5

This example illustrates the preparation of (2S,3R)-4-Dimethylamino-1,2-diphenyl-3-methyl-2-[1-(but-4-enyl) carbonyloxy]-butane, corresponding to formula (V) below, a precursor for preparation of a hapten of the invention.

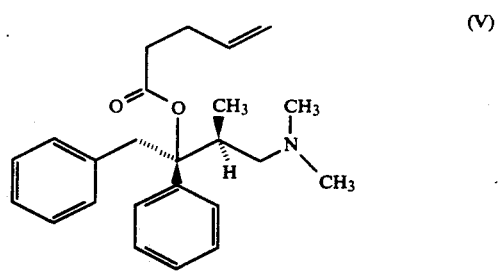

A solution of 153 mg (0.54 m mol) of the clear colorless oil (the alcohol) prepared in Example 1 above in a mixture of 1.0 ml benzene and 1.0 ml toluene was fractionally distilled, and only 1.0 ml of distillate was collected. The residual solution was cooled to ambient temperature, and a solution of 1.00 mmol of 4-pentenoyl chloride in benzene was added. The resulting mixture was gradually warmed; the benzene was removed by distillation; and the residual mixture was refluxed for 2 hr. The precipitate which formed was filtered and washed with 2 ml of toluene. The combined filtrate and washings were diluted in chloroform, extracted with 2M potassium hydroxide solution dried over MgSO4, filtered, and concentrated. The resulting olefinic ester was used without further purification.

EXAMPLE 6

This example illustrates the preparation of (2S,3R)-4-Dimethylamino-1,2-diphenyl-3-methyl-2-[1-(propan-3-al)carbonyloxy]-butane, corresponding to formula (VI) below, a hapten of the invention.

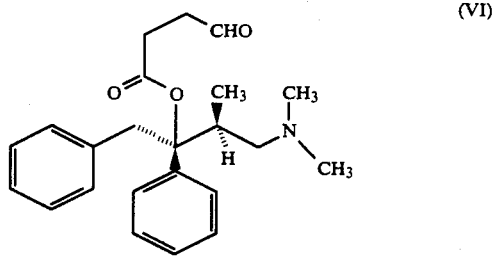

To a cooled (0°) solution of 40 mg (0.11 mmol) of the olefinic ester, prepared in Example 5 above, in 0.50 ml of dichloromethane, was added 50 μl of trifluoroacetic acid. The resulting mixture was stirred for 5 minutes after warming to ambient temperature, concentrated, and redissolved in 5.0 ml methanol. The resulting solution was ozonized until a blue color persisted. Excess ozone was removed by passage of a stream of argon, and the resulting colorless reaction mixture was quenched with 0.10 ml of dimethyl sulfide. The reaction mixture was warmed slowly to ambient temperature (over about 1 hr) and concentrated to provide 69 mg of a light-yellow oil of the hapten, (2S,3R)-4-Dimethylamino-1,2-diphenyl-3-methyl-2-[1-(propan-3-al)carbonyloxy]-butane. The hapten was conjugated to protein to produce an immunogen of the invention according to the procedure of Example 7 below.

EXAMPLE 7

This example illustrates the preparation of an immunogen of the invention illustrated in formula (VII) below in which BTG represents a bovine thyroglobulin moiety attached through an amide linkage to the remainder of the compound.

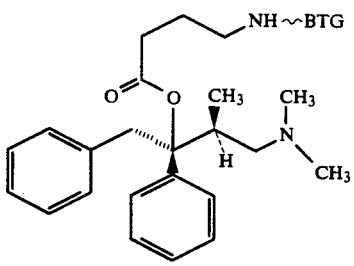
(VII)

(a) An amount of 53.0 mg of the hapten (VI) from example 6 was added to 1.0 ml of deionized water and 0.5 ml of dimethylsulfoxide (DMSO). A volume of 0.750 ml (containing 26.5 mg of hapten) of the resulting solution was added to 10.4 ml of a solution of bovine thyroglobulin (containing 10 mg/ml of thyroglobulin and 0.05 molar (M) sodium phosphate and having a pH=7.0) with stirring for 30 minutes at room temperature. Five additions of 50 mg each of sodium cyanoborohydride were added, with 2 hour intervals between additions, to the resulting mixture with the pH of the mixture having been adjusted with 0.1 normal (N) HCl to about 7.0 before each addition. After the last addition of sodium cyanoborohydride, the mixture was stirred for 2 hours. Next, the mixture was dialyzed in a cellulose dialyzing tube against 0.05M sodium phosphate at pH=7.5 for 36 hours with four changes of dialysate. After dialysis, the mixture was centrifuged in Sorvall at 10,000 revolutions per minute (rpm) for 10 minutes. The supernatant was found to contain 9.78 mg/ml of protein via the Lowry protein concentration determining method.

(b) Antisera was produced from the immunogen of part (a) immediately above and was utilized in fluorescence polarization immunoassays (FPIAs) directed to the determination of propoxyphene in urine samples.

The configuration of the reagents, calibrators and controls for the FPIAs is as follows:

1. The tracer formulation is 100 nanomolar tracer in: 0.1 molar sodium phosphate buffer at pH=6.3, 0.01 percent bovine gamma-globulin, 5 percent 5-sulfosalicylate, and 0.1 percent sodium azide.
2. The antiserum formulation comprises sheep serum diluted with: 0.1 molar tris buffer at pH=7.5, 2 percent ethylene glycol, 0.1 percent sodium azide, and 0.05 percent bovine gamma-globulin.
3. The pretreatment solution consists of: 0.1 molar tris buffer at pH=7.5, 0.01 percent bovine gamma-globulin, 0.1 percent sodium azide, and 4 mg/ml riboflavin binding protein.
4. The wash solution consists of: 0.1 molar sodium phosphate buffer at pH=7.5, 0.1 percent sodium azide, and 0.01 percent bovine gamma-globulin.
5. The dilution buffer consists of: 0.1 molar sodium phosphate buffer at pH=7.5, 0.1 percent sodium azide, and 0.01 percent bovine gamma-globulin.
6. The calibrator/control diluent consists of: normal human urine and 0.1 percent sodium azide.
7. Propoxyphene calibrators consist of propoxyphene in treated normal human urine at concentrations of 0.0, 150.0, 300.0, 500.0, 1000.0, and 1500.0 nanograms per milliliter.
8. Propoxyphene controls consist of: propoxyphene in treated normal human urine at concentrations of 200.0, 400.0 and 900.0 nanograms per milliliter.

(c) The assays used a six point calibration curve with dextropropoxyphene as the calibrator. The calibration curve has a two week minimum stability and a range of 0.0 ng/ml to 1500.0 ng/ml. The assays have a sensitivity of 20.0 ng/ml. Sensitivity is defined as the lowest measurable concentration which can be distinguished from zero with 95 percent confidence.

Reproducibility on the $TD_x$® instrument was determined on ten different days over a period of two weeks by assaying five replicates each of dextropropoxyphene in human urine at 200, 400 and 900 ng/ml. The concentration of each was determined from a single standard curve run on the first day of the study. The results are summarized in Table 1 below.

TABLE 1

| $TD_x$ ® DATA | Concentration (ng/ml) | | |
|---|---|---|---|
| Target Value | 200 | 400 | 900 |
| No. Samples = 50 | | | |
| Mean | 187.85 | 388.27 | 887.33 |
| SD Within Run | 2.87 | 6.38 | 12.88 |
| CV Within Run (%) | 1.53 | 1.64 | 1.45 |
| SD Between Run | 9.30 | 15.70 | 25.55 |
| CV Between Run (%) | 4.95 | 4.04 | 2.88 |
| SD Total | 9.73 | 16.95 | 28.61 |
| CV Total (%) | 5.18 | 4.37 | 3.22 |

Reproducibility on the $AD_x$® instrument was determined over fifteen different runs, in combination, batch and panel modes, by assaying four replicates each of dextropropoxyphene in human urine at 200, 400, and 900 ng/ml. The concentration of each was determined from a standard curve run in duplicate on the first day of the study. The results are summarized in TABLE 2 below

TABLE 2

| $AD_x$ ® DATA | Concentration (ng/ml) | | |
|---|---|---|---|
| Target Value | 200 | 400 | 900 |
| No. Samples = 60 | | | |
| Mean | 195 | 401 | 906 |
| SD Within Run | 4.55 | 10.47 | 19.42 |
| CV Within Run (%) | 2.34 | 2.61 | 2.14 |
| SD Between Run | 9.71 | 11.94 | 29.10 |
| CV Between Run (%) | 4.99 | 2.98 | 3.21 |
| SD Total | 10.72 | 15.88 | 34.98 |
| CV Total (%) | 5.51 | 3.96 | 3.86 |

Two sets of calibrators and controls were prepared by adding known quantities of dextropropoxyphene to human urine and X Systems Dilution Buffer to levels of 150, 200, 300, 400, 500, 900, 1000 and 1500 ng/ml. A calibration was run with urine calibrators and both sets of calibrators were assayed relative to this calibration. In the following Table 3, "% Recovery" equals 100× (measured concentration in buffer divided by measured concentration in urine).

TABLE 3

| Target Concentration (ng/ml) | Concentration in Buffer (ng/ml) | Concentration in Urine (ng/ml) | % Recovery |
|---|---|---|---|
| 150 | 155.87 | 157.97 | 98.7 |
| 200 | 208.46 | 199.91 | 104.3 |
| 300 | 290.89 | 287.74 | 101.1 |
| 400 | 392.98 | 401.29 | 97.9 |
| 500 | 506.07 | 493.98 | 102.4 |
| 900 | 932.92 | 901.39 | 103.5 |
| 1000 | 1020.65 | 1003.00 | 101.8 |

TABLE 3-continued

| Target Concentration (ng/ml) | Concentration in Buffer (ng/ml) | Concentration in Urine (ng/ml) | % Recovery |
| --- | --- | --- | --- |
| 1500 | 1447.40 | 1489.22 | 97.2 |

Average Recovery = 100.9 plus or minus 2.6%

Various test compounds were assayed (to determine cross-reactivity) with the dextropropoxyphene assay after a known quantity of the test compound was added to drug-free human urine and In the following Tables 4 and 5, "% Cross-Reactivity" equals 100× ("Concentration Found" divided by the "Concentration Added"). Cross-reactivity was tested for nordextropropoxyphene (N-Norpropoxyphene). The results for dextropropoxyphene, is summarized in Table 4 below. From the results in Table 4, it can be seen that the invention can provide immunoassays having advantageously high-cross reactivity for nordextropropoxyphene (NDP).

TABLE 4

CROSS-REACTIVITY/NORDEXTROPROPOXYPHENE

| Test Compound | Concentration Added (ng/ml) | Concentration Found (ng/ml) | % Cross-Reactivity |
| --- | --- | --- | --- |
| NDP | 1,500 | 445.13 | 29.7 |
| NDP | 1,000 | 394.62 | 39.5 |
| NDP | 400 | 235.78 | 58.9 |
| NDP | 300 | 204.67 | 68.2 |
| NDP | 200 | 160.39 | 80.2 |

Cross-reactivities likewise were measured for compounds (interferants) that have similar chemical structure or are used concurrently by humans. The results are summarized in the following Table 5. In Table 5, "ND*" means "None Detected" meaning that the concentration is less than the sensitivity of the assay. From Table 5 it can be seen that the invention can provide immunoassays having advantageously low cross-reactivity for potential interferants.

TABLE 5

CROSS-REACTIVITIES/INTERFERANTS

| Test Compound | Concentration Added (ng/ml) | Concentration Found (ng/ml) | % Cross-Reactivity |
| --- | --- | --- | --- |
| Amitriptylene | 1,000,000 | 228.81 | <0.1 |
| " | 100,000 | 74.75 | <0.1 |
| " | 50,000 | 54.50 | 0.1 |
| " | 10,000 | ND* | — |
| Brompheniramine | 100,000 | 56.84 | <0.1 |
| " | 50,000 | 40.89 | <0.1 |
| Chlorpheniramine | 1,000,000 | 130.50 | <0.1 |
| " | 100,000 | ND* | — |
| Chlorpromazine | 100,000 | 101.59 | 0.1 |
| " | 50,000 | 76.35 | 0.2 |
| " | 10,000 | ND* | — |
| Clemastine | 100,000 | 59.53 | <0.1 |
| " | 50,000 | ND* | — |
| Cyclizine | 100,000 | 48.03 | <0.1 |
| Diphenhydramine | 100,000 | 56.01 | <0.1 |
| " | 50,000 | ND* | — |
| Ethinyl Estradiol | 100,000 | 46.78 | <0.1 |
| Fluoxetine | 1,000,000 | 294.35 | <0.1 |
| " | 100,000 | 113.22 | 0.1 |
| " | 50,000 | 79.83 | 0.2 |
| " | 10,000 | ND* | — |
| Methadone | 100,000 | 50.93 | <0.1 |
| " | 50,000 | ND* | — |

TABLE 5-continued

CROSS-REACTIVITIES/INTERFERANTS

| Test Compound | Concentration Added (ng/ml) | Concentration Found (ng/ml) | % Cross-Reactivity |
| --- | --- | --- | --- |
| Methapyrilene | 100,000 | 44.96 | <0.1 |
| Promethazine | 100,000 | 46.07 | <0.1 |
| " | 50,000 | ND* | — |
| Trihexyphenidyl | 100,000 | 53.54 | <0.1 |
| " | 50,000 | 49.04 | <0.1 |
| " | 10,000 | ND* | — |
| Tripelennamine | 1,000,000 | 155.73 | <0.1 |
| " | 100,000 | 47.21 | <0.1 |
| " | 50,000 | ND* | — |

What is claimed is:

1. A substantially optically pure hapten, useful in an immunoassay for dextropropoxyphene and/or nordextropropoxyphene, said hapten corresponding to the formula (IX):

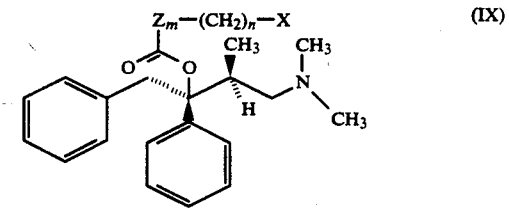

(IX)

wherein
Z is —NH—;
X is —CHO, —COOH, —NH$_2$, or —COOR in which R is a C$_1$–C$_3$ alkyl group;
m is 0 or 1; and
n is an integer of from 1 to 3.

2. The hapten of claim 1 wherein m=0 and n=3.

3. The hapten of claim 2 wherein X is —CHO.

4. A fluorescent tracer derived from a substantially optically pure compound, said tracer being useful in an immunoassay for dextropropoxyphene and/or nordextropropoxyphene and corresponding to the formula (XI):

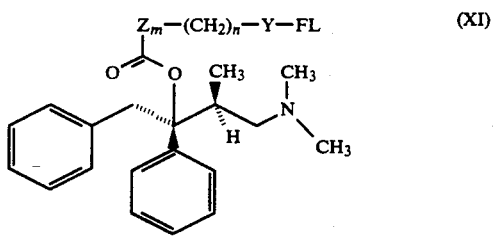

(XI)

wherein
Z is —NH—;
Y is —NH—, —(CO)NH—, or —NH(CO)—;
m is 0 or 1;
n is an integer of from 1 to 3; and
FL is a fluorescence-conferring moiety.

5. The fluorescent tracer of claim 4 wherein m=1 and n=1.

6. The fluorescent tracer of claim 5 wherein Y is —(CO)NH—.

7. The fluorescent tracer of claim 4 wherein said fluorescence-conferring moiety is a monovalent residue of fluorescein or a monovalent residue of a fluorescein derivative.

* * * * *